United States Patent [19]

Bott

[11] Patent Number: 5,041,649

[45] Date of Patent: Aug. 20, 1991

[54] PREPARATION OF CARBONYL HALIDES

[75] Inventor: Kaspar Bott, Mannheim, Fed. Rep. of Germany

[73] Assignee: BASF Aktiengesellschaft, Ludwigshafen, Fed. Rep. of Germany

[21] Appl. No.: 68,013

[22] Filed: Jun. 29, 1987

[30] Foreign Application Priority Data

Jul. 11, 1986 [DE] Fed. Rep. of Germany ....... 3623422

[51] Int. Cl.$^5$ ...................... C07C 51/58; C07C 53/42; C07C 53/44; C07C 53/50
[52] U.S. Cl. .................................. 562/848; 260/408; 562/840; 562/849; 562/867
[58] Field of Search .......................... 260/408, 544 A; 562/848, 849, 840, 867

[56] References Cited

U.S. PATENT DOCUMENTS

| | | | |
|---|---|---|---|
| 2,378,048 | 6/1945 | Theobald | 562/848 |
| 2,411,982 | 12/1946 | Theobald | 562/848 |
| 3,471,557 | 10/1969 | Coffield et al. | 260/544 |

FOREIGN PATENT DOCUMENTS 3128445 2/1983 Fed. Rep. of Germany .

Primary Examiner—Vivian Garner
Attorney, Agent, or Firm—John H. Shurtleff

[57] ABSTRACT

Carbonyl halides I

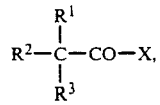

where
$R^1$ is H, alkyl, cycloalkyl, haloalkyl or halocycloalkyl,
$R^2$ and $R^3$ are each alkyl, cycloalkyl, haloalkyl or halocycloalkyl and may furthermore be bonded to one another to form a 5-membered to 7-membered ring and
is halogen,
are prepared by reacting an alkyl halide II

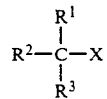

with carbon monoxide under superatmospheric pressure in the presence of a catalytic amount of
a) aluminum bromide and in the presence or absence of a solvent or
b) aluminum chloride or bromide and in the presence of a halohydrocarbon and a carbonyl halide of the formula III

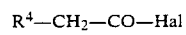 (III)

where $R^4$ is hydrogen or $C_1$-$C_4$-alkyl and Hal is halogen.

13 Claims, No Drawings

PREPARATION OF CARBONYL HALIDES

The present invention relates to an improved process for the preparation of carbonyl halides by reacting a secondary or tertiary alkyl halide with carbon monoxide under superatmospheric pressure in the presence of a catalytic amount of a Lewis acid and in the presence or absence of a solvent.

German Laid-Open Application DOS 3,128,445 discloses that secondary or tertiary alkyl halides can be reacted with carbon monoxide in the presence of aluminum chloride or iron chloride as a catalyst to give the corresponding acyl halides without equimolar amounts of catalyst being required. Good yields and selectivities are obtained in particular in the presence of aluminum chloride, so that the use of this catalyst appears to be essential to the success of this process, at all events when no other Brönsted or Lewis acids are used. The use of aluminum chloride is disadvantageous in that it is only poorly soluble in many solvents preferred for Friedel-Crafts syntheses, e.g. methylene chloride, chloroform, tetrachloroethylene or trichlorobenzene. On the other hand, solvents in which aluminum chloride is readily soluble, such as nitrobenzene or sulfolane, deactivate the catalyst.

For a continuous reaction procedure, which is preferred in industry, it is important for a catalyst to be capable of being fed into the pressure reactor not in solid form but in solution, and of course its activity should not be reduced.

It is an object of the present invention to provide a catalyst which does not have the disadvantages described.

We have found that this object is achieved by a process for the preparation of carbonyl halides of the formula I

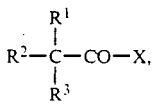

where $R^1$ is hydrogen, alkyl, cycloalkyl, haloalkyl or halocycloalkyl, $R^2$ and $R^3$ are each alkyl, cycloalkyl, haloalkyl or halocycloalkyl and may furthermore be bonded to one another to form a 5-membered to 7-membered ring, and X is halogen, by reacting an alkyl halide of the formula II

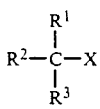

with carbon monoxide under superatmospheric pressure in the presence of a catalytic amount of a Lewis acid, wherein the reaction is carried out in the presence of
a) aluminum bromide as a catalyst or
b) aluminum bromide or chloride as a catalyst and in the presence of a halohydrocarbon and a carbonyl halide of the formula III

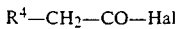

where $R^4$ is hydrogen or $C_1$-$C_4$-alkyl and Hal is halogen.

The aluminum bromide, which is advantageously used in a concentration of from 0.005 to 0.05 mole per mole of alkyl halide II, is readily soluble in the solvents, such as halohydrocarbons, which are particularly suitable for the reaction. Examples of halohydrocarbons are bromohydrocarbons, preferably chlorohydrocarbons, in particular chloroalkanes, chloroalkenes, chlorocycloalkanes or chlorobenzene. Specific examples are methylene chloride, chloroform, tri- and tetrachloroethane, tetrachloroethylene, hexachlorobutadiene and mono-, di- and trichlorobenzene. Chloroalkanes and chloroalkenes, in particular those of 1 to 4 carbon atoms, are particularly preferably used, methylene chloride and tetrachloroethylene being preferred. However, the reaction can also be carried out in the absence of a solvent if the alkyl halide II is liquid at the chosen reaction temperature.

The solubility of the aluminum bromide in the stated solvents, which in any case is good, can be further increased if carbonyl halides of the formula $R^4$—$CH_2$—CO—Hal, where $R^4$ is hydrogen or $C_1$-$C_4$-alkyl and Hal is halogen, in particular chlorine or bromine, are added as a solubilizing component. $C_2$- and $C_3$-acyl halides, e.g. acetyl and propionyl chloride, are particularly suitable. The addition of these solubilizers also makes it possible to use aluminum chloride as a catalyst without solubility problems being encountered.

The amount of acyl halides can be about 0.1-2 moles per mole of aluminum halide. Preferably, from 0.1 to 1.5, in particular from 0.3 to 1.3, moles of acyl halide are used per mole of aluminum bromide, and from 0.5 to 1.8, in particular from 0.8 to 1.5, moles of acyl halide per mole of aluminum chloride.

The addition of the acyl halide does not result in any significant decrease in catalyst activity and no decarbonylation occurs, as may be the case, for example, when the products formed in the reaction are used as solubilizers.

Suitable starting materials II are alkyl halides in which the halogen atom X is, for example, fluorine, chlorine or bromine. It is advantageous to react alkyl bromides, and particularly advantageous to react alkyl chlorides. $R^1$ is hydrogen or branched or preferably straight-chain alkyl which is unsubstituted or substituted by one or more halogen atoms, such as fluorine or in particular chlorine or bromine. Alkyl is, for example, of 1 to 20, preferably 1 to 10, in particular 1 to 5, carbon atoms. Specific examples of radicals $R^1$ are methyl, ethyl, propyl, isopropyl, butyl, isobutyl, amyl, isoamyl, hexyl, octyl and dodecyl, and specific examples of halogen-substituted alkyl radicals are chloromethyl, bromomethyl, fluoromethyl and ethyl, propyl, butyl, amyl, hexyl, heptyl, octyl, decyl or dodecyl, each of which is substituted by fluorine, chlorine or bromine.

$R^1$ may furthermore be cycloalkyl, preferably of 5 or 6 carbon atoms, which is unsubstituted or substituted by one or more of the abovementioned halogen atoms. Specific examples are cyclobutyl, cyclopentyl, cyclohexyl, methylcyclohexyl, chlorocyclopentyl, chlorocyclohexyl, bromocyclopentyl and bromocyclohexyl.

Apart from hydrogen, $R^2$ and $R^3$ have the meanings stated for $R^1$. Together with the carbon atom to which they are bonded, they may furthermore form a ring system which may also be bridged. In general, they are bonded to one another to form a 5-membered to 7-membered ring. Specific examples are the cyclopentyl, cyclohexyl, cycloheptyl, bicyclo[2,2,1]heptyl, bicyclo[2,2,2]octyl and bicyclo[3,2,1]octyl system. The stated cycloalkyl radicals may furthermore be substituted by $C_1$-$C_4$-alkyl.

For example, the following starting materials may be used for the reaction: tert-butyl chloride and bromide, tert-amyl chloride and bromide, 1,2-dichloro-2-methylpropane, 2-chloro-2-methylhexane, 2-bromo-2-methylhexane, 2-chloro-2-propylhexane, 1-chloro-1-methylcyclohexane, norbornyl chloride and norbornyl bromide.

The reaction is carried out batchwise or, preferably, continuously in a conventional manner under a carbon monoxide pressure of about 10–500, preferably 50–400, in particular 150–300, bar and at from $-20$ to $+80°$ C., preferably from 0 to 40° C., in particular from 0 to 10° C., the optimum reaction temperature depending to a great extent on the starting material II and the solvent used. The amount of solvent can be, for example, from 10 to 500, in particular from 20 to 100, advantageously from 20 to 50, % by volume, based on the volume of the alkyl halide used.

When the reaction is complete, the pressure can be let down to atmospheric pressure as in conventional processes, so that the product I formed, unconverted starting material II and any solvent present can be separated off from the catalyst. However, there is a danger that some of the carbonyl halide will be decomposed in a reaction which is the reverse of that in which it is formed. This decomposition can be substantially avoided if, before the pressure is let down, a carboxamide is added to the reaction mixture in order to destroy the Lewis acid catalyst. Acid amides of low molecular weight carboxylic acids, which can readily be separated from the reaction mixture, e.g. amides of $C_1$-$C_5$-carboxylic acids, such as formic acid, acetic acid, propionic acid, butyric acid or valeric acid, are preferably used. A particularly preferred acid amide is dimethylformamide. To destroy the catalyst completely, equimolar amounts of the acid amide are added to the aluminum halide. Smaller or larger amounts are possible but are of no advantage.

Working up the reaction mixture by distillation is carried out in a conventional manner and therefore need not be described.

EXAMPLES 1 TO 3

The aluminum bromide, with or without the solvent or solubilizer, is initially taken in a stirred autoclave at $+5°$ C. Thereafter, carbon monoxide was forced in to give a pressure of 200 bar, the alkyl chloride was pumped in over from 30 to 80 minutes, and the CO pressure was increased to 300 bar. The reaction mixture was then left to react for from 10 to 12 hours at the stated temperature, the CO pressure being kept constant at 300 bar.

Working up was carried out by adding an equimolar amount, based on the aluminum bromide, of dimethylformamide to the reaction mixture before the pressure is let down, and distilling off the reacted mixture from the catalyst under reduced pressure. The yields determined by gas chromatographic analysis of the distillate and details of the reaction are shown in the Table below.

TABLE

| | | | $RCl + CO \xrightarrow{AlBr_3} R\text{-}CO\text{-}Cl$ | | | |
|---|---|---|---|---|---|---|
| Example | RCl g/mol | $AlBr_3$ g/mol | Solvent g | Reaction at T = °C. | Yield[a] g/% | Selectivity[a] % |
| 1 | exo-norbornyl chloride 132/1.01 | 7/0.026 | — | 5–10 | 152/88[b] | |
| 2 | tert-butyl chloride 600/6.48 | 20/0.075 | tetrachloroethylene 162 | 2–3 | 667/85.3 | 96.5 |
| 3 | tert-butyl chloride 600/6.48 | 30/0.11 | dichloromethane/ acetyl chloride 133/8.8 | 2–3 | 682/87.3 | 96.6 |

[a]based on starting materials RCl
[b]8.8 g of exo-norbornanecarbonyl bromide in addition = 4.3% yield[d]

I claim:

1. In a process for the preparation of a carbonyl halide of the formula

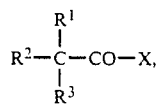

where $R^1$ is hydrogen, alkyl, cycloalkyl, haloalkyl or halocycloalkyl, $R^2$ and $R^3$ are each alkyl, cycloalkyl, haloalkyl or halocycloalkyl and may furthermore be bonded to one another to form a 5-membered to 7-membered ring, and X is halogen, by reacting the corresponding halide of the formula

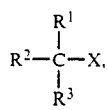

wherein $R^1$, $R^2$ and $R^3$ have the same meanings given above, with carbon monoxide under superatmospheric pressure in the presence of a catalytic amount of a Lewis acid, the improvement which comprises:
carrying out the reaction in the presence of aluminum bromide or chloride as a catalyst and in the further presence of a halohydrocarbon solvent and, as a solubilizer, a carbonyl halide of the formula

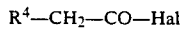

where $R^4$ is hydrogen or $C_1$-$C_4$-alkyl and Hal is halogen.

2. A process as claimed in claim 1, wherein the catalyst consists essentially of aluminum chloride used in an amount of from 0.005 to 0.05 mole per mole of the halide reactant II, and the reaction is carried out at a temperature of from $-20$ to $+80°$ C., under a carbon monoxide pressure of about 10 to 500 bar, and in the presence of a halohydrocarbon solvent and in the further presence of the carbonyl halide III as a solubilizer.

3. A process as claimed in claim 2, wherein the halohydrocarbon solvent is used in an amount of from 10 to 500% by volume, based on the volume of the halide reactant II, and the carbonyl halide solubilizer III is used in an amount of from 0.1 to 2 moles per mole of aluminum chloride.

4. A process as claimed in claim 3, wherein the carbonyl halide solubilizer III is selected from the group consisting of acetyl and propionyl chloride.

5. A process as claimed in claim 1, wherein the aluminum bromide or chloride catalyst is used in an amount of from 0.005 to 0.05 mole per mole of the halide reactant II.

6. A process as claimed in claim 1, wherein a chlorohydrocarbon is used as the solvent.

7. A process as claimed in claim 1, wherein a chloroalkane is used as the solvent.

8. A process as claimed in claim 1, wherein the carbonyl halide III, as a solubilizer, is used in an amount of from 0.1 to 2 moles per mole of the aluminum bromide or chloride.

9. A process as claimed in claim 8, wherein acetyl or propionyl chloride is used as the carbonyl halide III.

10. A process as claimed in claim 1, wherein the initial reactant II is an alkyl chloride or bromide.

11. A process as claimed in claim 1, wherein the reaction is carried out at from 10 to 500 bar.

12. A process as claimed in claim 1, wherein the catalyst is destroyed when the reaction is complete by adding a carboxamide.

13. A process as claimed in claim 1, wherein the alkyl halide reactant II is tert.-butyl chloride or bromide.

* * * * *

UNITED STATES PATENT AND TRADEMARK OFFICE
CERTIFICATE OF CORRECTION

PATENT NO. : 5,041,649
DATED : August 20, 1991
INVENTOR(S) : Kaspar Bott

It is certified that error appears in the above-identified patent and that said Letters Patent is hereby corrected as shown below:

On the title page:
IN THE ABSTRACT:

In column 2, after the formula, at line 7 of the text, please insert "X" before "is halogen,".

Signed and Sealed this

Third Day of November, 1992

Attest:

DOUGLAS B. COMER

Attesting Officer     Acting Commissioner of Patents and Trademarks